United States Patent [19]

Morris

[11] Patent Number: 4,726,368

[45] Date of Patent: Feb. 23, 1988

[54] NON-REFLECTIVE SURGICAL INSTRUMENTS

[75] Inventor: James R. Morris, Houston, Tex.

[73] Assignee: Bioquantum Technologies, Inc., Houston, Tex.

[21] Appl. No.: 914,533

[22] Filed: Oct. 1, 1986

Related U.S. Application Data

[63] Continuation of Ser. No. 702,690, Feb. 19, 1985, abandoned, which is a continuation-in-part of Ser. No. 582,704, Feb. 23, 1984, abandoned.

[51] Int. Cl.$^4$ .............................................. A61B 17/00
[52] U.S. Cl. .................................. 128/303 R; 128/339
[58] Field of Search ............................ 428/469; 427/2; 148/6.2; 128/339, 335.5, 303 R

[56] References Cited

U.S. PATENT DOCUMENTS

| | | | |
|---|---|---|---|
| 2,667,456 | 1/1954 | Young | 148/6.2 |
| 2,865,375 | 12/1958 | Banks et al. | 128/339 |
| 2,865,376 | 12/1958 | Pellier et al. | 128/339 |
| 2,917,817 | 12/1959 | Tabor | 428/469 |
| 2,975,078 | 3/1961 | Rayfield | 428/469 |
| 3,005,729 | 10/1961 | Tucker et al. | 148/6.2 |
| 3,210,220 | 10/1965 | Clegg et al. | 148/6.21 |
| 3,480,483 | 11/1969 | Wilkinson | 428/469 |
| 3,721,534 | 3/1973 | Kubick | 428/469 |
| 3,892,883 | 7/1975 | Leclercq | 428/469 |
| 4,026,737 | 5/1977 | Takahari et al. | 148/6.2 |
| 4,122,853 | 10/1978 | Smith | 128/303.1 |
| 4,312,915 | 1/1982 | Fan | 428/469 |
| 4,314,005 | 2/1982 | Arias | 428/469 |
| 4,378,796 | 4/1983 | Milhand | 128/207.15 |
| 4,483,899 | 11/1984 | Kuwabara | 428/469 |
| 4,497,877 | 2/1985 | Krijl et al. | 428/469 |
| 4,518,467 | 5/1985 | Mason et al. | 428/469 |

FOREIGN PATENT DOCUMENTS

| | | | |
|---|---|---|---|
| 45-19368 | 2/1970 | Japan | 148/6.2 |
| 1387333 | 3/1975 | United Kingdom | 148/6.2 |

OTHER PUBLICATIONS

The Surgical Armamentarium, American V. Mueller, 1980, p. 1268.

Primary Examiner—C. Fred Rosenbaum
Assistant Examiner—Gene B. Kartchner
Attorney, Agent, or Firm—Arnold, White & Durkee

[57] ABSTRACT

A non-reflective instrument comprising a metallic substrate and a coating selected from the group consisting of $Al_2O_3$, $Al_2O_3/TiO$ mixtures, $Al_2O_3/Cr_3O_2$ mixtures and WC/Co mixtures.

3 Claims, No Drawings

NON-REFLECTIVE SURGICAL INSTRUMENTS

CROSS REFERENCE TO RELATED APPLICATIONS

This application is a continuation of application Ser. No. 702,690, filed Feb. 19, 1985, now abandoned, which is a continuation-in-part of application Ser. No. 582,704, filed 2/23/84, now abandoned.

FIELD OF THE INVENTION

This invention relates to instruments and tools for use in procedures where a laser beam is used for the cutting, fusing, or other processing of materials. In particular, the invention is directed to non-reflective surgical instruments for use in laser surgery.

BACKGROUND OF THE INVENTION

The use of lasers in surgery has grown dramatically in the past ten years. In particular, the use of the $CO_2$ laser in surgery has grown from a very limited range of applications in the mid-1970s to become a widely used tool for a variety of surgical procedures in virtually every major surgical specialty. During this time, however, the instruments used by surgeons in conjunction with lasers, such as forceps and clamps, remained essentially unchanged.

In addition to medical applications, lasers are increasingly used in various manufacturing procedures. For example, lasers can be used for welding in the assembly of micro-electronic components. Special tools are often required in such procedures.

Instruments used in laser surgery are in most respects of the same type as those used in more conventional surgery. However, special properties are required of instruments used in laser surgery. One of the principle requirements is that the instrument not reflect the laser beam if the beam inadvertently or unavoidably strikes the instrument. If the laser beam is reflected, there is the likelihood that the patient or even the surgeon or his assistants may be injured by the reflected beam. This non-reflective requirement makes standard stainless steel surgical instruments unsuited for laser surgery.

Previously, attempts have been made to manufacture instruments which were both non-reflective and still functional in their intended use. Glass instruments, which absorb the infrared radiation used in laser surgery, have been tried without success. Under the heat loads generated by the laser beam, glass instruments are prone to cracking and breaking leading to the dangerous possibility of portions of the instrument being lost within the incision. In addition, sturdy glass instruments are difficult to fabricate in the variety of intricate shapes required for the various surgical techniques.

Wooden instruments have also been used in laser surgery. Aside from the difficulty of fabricating complex instruments, the danger of fire exists when wooden instruments are exposed to an infrared laser beam. Other materials have been tested, including specially annealed glasses, plastics, oxidized and dioxidized metals. These materials have been found lacking due to poor mechanical or chemical characteristics.

Perhaps the most successful, to date, non-reflective instruments are anodized stainless steel or titanium instruments. These instruments, although the best current alternatives and widely used, suffer a number of serious drawbacks. The anodized coating scratches easily and small portions of it can be left in the wound. Anodization is an oil base process and toxic fumes generated when the instrument is subjected to the high temperatures generated by the laser beam are a hazard. Anodization reduces reflection by only 45% to 50% and the reflected beam is not diffused in nature. Even if the instrument is sand blasted prior to anodization, the anodization process glazes over the surface and the reflected beam is specular in nature.

In summary, a suitable instrument for laser surgery must be non-reflective and possess sufficient structural and chemical integrity to withstand the demands placed upon it by the surgeon's manipulations, the heat generated by the laser beam, and the normal wear and tear of hospital cleaning and sterilizing. In addition, it is desirable that the instrument possess a similar heft and balance to conventional instruments so that the surgeon feels comfortable in using the instrument.

Tools and instruments for use in non-medical applications must exhibit similar properties. The tools must be non-reflective and at the same time retain their ability to function in their intended use.

The instruments of the present invention are the first instruments to meet these requirements. They are non-reflective and still retain their inherent value as tools. The instruments of the instant invention are resistant to corrosion, have good wear properties, high mechanical strength at high temperatures and are easily sterilized. They may be fabricated in any of the myriad of shapes and forms required. Finally, there is little difference, if any, in the feel of these new instruments when compared to conventional surgical instruments.

SUMMARY OF THE INVENTION

The present invention involves non-reflective instruments for use in laser processes. The instruments are made of metallic substrate and a non-reflective coating of a material which adsorbs radiation in the infrared region and is selected from the group consisting of aluminum oxide ($Al_2O_3$), aluminum oxide-titanium oxide mixtures ($Al_2O_3$-TiO), chromium oxide-aluminum oxide mixtures and tungstencarbide-cobalt mixtures (WC/Co).

DETAILED DESCRIPTION

The present invention is applicable to almost any surgical instrument that might be used in laser surgery. Typical examples of such instruments include: forceps, clamps, retractors, elevators, suctions, nerve hooks, separators, microinfertility instruments, needle holders, currettes, etc. In addition, as new instruments are developed for specialized techniques, the same inventive concept will allow their adoption for laser surgery.

The instruments of the instant invention have a metallic substrate and are coated to render the instruments non-reflective. The underlying instrument or substrate will typically be stainless steel or titanium. The requirements for the substrate material are generally the same as those utilized in designing conventional instruments. For example, many instruments must possess a degree of springiness to operate properly. The instruments of the present invention may be manufactured starting with existing conventional instruments as the metallic substrate.

The coating of the instrument must possess, as its principal property, the ability to absorb infrared radiation. The coating must also adhere strongly to the substrate.

Tables I–III report reflectance of $CO_2$ laser energy by various materials at three different angles of incidence. In all cases except the anodized aluminum, the substrate was stainless steel. The low incident angle of Table I is approximately 10°; the intermediate incident angle of Table II is approximately 45°; and the high incident angle of Table III is 75°. As is seen, the order of effectiveness of the various materials varies to a certain extent dependent on the incident angle. However, in each case the $Al_2O_3/TiO$ mixture is superior. As can be seen from the two $Al_2O_3$ coatings, the detonation gun process is superior to the plasma torch process.

TABLE I
LOW INCIDENT ANGLE

| Material | Commercial Designation[1] | Coating[2] Method | Coating[3] Thickness | P in[4] (watts) | P out (watts) | % Reflected | Ranking |
|---|---|---|---|---|---|---|---|
| $Al_2O_3$ | LA-2 | D-Gun | <.002 | 5.0 | .006 | .12 | 2 |
|  |  |  | <.004 | 5.05 | .006 | .12 |  |
| $Al_2O_3$ | LA-6 | Plasma |  | 5.25 | .011 | .21 | 4 |
| $Al_2O_3/TiO$[5] | LA-7 | D-Gun | <.002 | 5.38 | .003 | .06 | 1 |
|  |  |  | <.004 | 5.75 | .005 | .09 |  |
| $Cr_2O_3$ | LC-4 | Plasma | <.002 | 5.70 | .072 | 1.26 | 8 |
|  |  |  | <.004 | 6.00 | .061 | 1.02 |  |
| $Cr_2O_3/Al_2O_3$[6] | LC-19 | Plasma | <.002 | 6.00 | .010 | .17 | 3 |
|  |  |  | <.004 | 6.05 | .012 | .20 |  |
| WL/Co[7] | LW-1N30 | D-Gun | <.002 | 6.10 | .035 | .57 | 7 |
|  |  |  | <.004 | 6.10 | .031 | .51 |  |
| Anodized Al | — | — | — | 5.9 | .015 | .25 | 5 |
| AVM[8] | — | — | — | 6.0 | .025 | .42 | 6 |
| Stainless Steel | — | — | — | 5.1 | 4.7 | 92.2 | 9 |

TABLE II
INTERMEDIATE INCIDENT ANGLE

| Material | Commercial Designation[1] | Coating[2] Method | Coating[3] Thickness | P in[4] (watts) | P out (watts) | % Reflected | Ranking |
|---|---|---|---|---|---|---|---|
| $Al_2O_3$ | LA-2 | D-Gun | <.002 | 5.85 | .100 | 1.71 | 3 |
|  |  |  | <.004 | 5.90 | .105 | 1.78 |  |
| $Al_2O_3$ | LA-6 | Plasma |  | 5.95 | .220 | 3.70 | 5 |
| $Al_2O_3/TiO$[5] | LA-7 | D-Gun | <.002 | 5.90 | .040 | .68 | 1 |
|  |  |  | <.004 | 5.90 | .035 | .59 |  |
| $Cr_2O_3$ | LC-4 | Plasma | <.002 | 5.85 | .590 | 10.09 | 8 |
|  |  |  | <.004 | 5.85 | .480 | 8.21 |  |
| $Cr_2O_3/Al_2O_3$[6] | LC-19 | Plasma | <.002 | 5.85 | .132 | 2.26 | 4 |
|  |  |  | <.004 | 5.85 | .134 | 2.29 |  |
| WC/Co[7] | LW-1N30 | D-Gun | <.002 | 5.80 | .093 | 1.60 | 2 |
|  |  |  | <.004 | 5.80 | .095 | 1.64 |  |
| Anodized Al | — | — | — | 5.75 | .490 | 8.52 | 7 |
| AVM[8] | — | — | — | 5.75 | .290 | 5.04 | 6 |
| Stainless Steel | — | — | — | 6.0 | 4.7 | 78.3 | 9 |

TABLE III
HIGH INCIDENT ANGLE

| Material | Commercial Designation[1] | Coating[2] Method | Coating[3] Thickness | P in[4] (watts) | P out (watts) | % Reflected | Ranking |
|---|---|---|---|---|---|---|---|
| $Al_2O_3$ | LA-2 | D-Gun | <.002 | 5.25 | .220 | 4.19 | 2 |
|  |  |  | <.004 | 5.20 | .160 | 3.08 |  |
| $Al_2O_3$ | LA-6 | Plasma |  | 5.25 | .700 | 13.33 | 5 |
| $Al_2O_3/TiO$[5] | LA-7 | D-Gun | <.002 | 5.07[9] | .111[9] | 2.21[9] | 1 |
|  |  |  | <.004 | 4.98[9] | .069[9] | 1.39[9] |  |
| $Cr_2O_3$ | LC-4 | Plasma | <.002 | 5.05 | 1.38 | 27.33 | 8 |
|  |  |  | <.004 | 5.05 | 1.20 | 23.76 |  |
| $Cr_2O_3/Al_2O_3$[6] | LC-19 | Plasma | <.002 | 4.80 | .640 | 13.33 | 4 |
|  |  |  | <.004 | 5.00 | .580 | 11.60 |  |
| WC/Co[7] | LW-1N30 | D-Gun | <.002 | 4.95 | .230 | 4.65 | 3 |
|  |  |  | <.004 | 4.85 | .175 | 3.61 |  |
| Anodized Al | — | — | — | 5.80 | 1.400 | 24.14 | 7 |
| AVM[8] | — | — | — | 4.90 | .950 | 19.39 | 6 |
| Stainless Steel | — | — | — | 5.85 | 5.600 | 95.73 | 9 |

[1] Designations of Union Carbide Corporation.
[2] Union Carbide Detonation Gun and Plasma Torch coating methods.
[3] <.002 designates coating between approximately .001–.002" thick; <.004 designates coating between approximately .002–.004" thick.
[4] $CO_2$ laser beam, 10.6 micron wavelength.
[5] 60% $Al_2O_3$, 40% TiO.
[6] 70% $Cr_2O_3$, 30% $Al_2O_3$.
[7] 87% WC, 13% Co.
[8] Commercial non-reflective instrument marketed by American V. Mueller.
[9] Average of two values.

In order to evaluate the overall effectiveness of each material, a composite ranking was calculated by averaging the ranking of each material at each incidence angle. The data demonstrates that $Al_2O_3$, $Al_2O_3/TiO$, $Cr_2O_3/Al_2O_3$, and WC/Co all perform, on average, significantly better than the prior art and better than the currently available coated instruments. The detonation gun deposited $Al_2O_3$ and $Al_2O_3/TiO$ coatings are the preferred materials. The 60% $Al_2O_3$/40% TiO coating is particularly preferred.

TABLE IV
COMPOSITE RANKINGS

| Material | Commercial Designation | Composite Ranking |
|---|---|---|
| $Al_2O_3/TiO$ | LA-7 | 1.0 |
| $Al_2O_3$ | LA-2 | 2.3 |
| $Cr_2O_3/Al_2O_3$ | LC-19 | 3.6 |
| WC/Co | LW-1N30 | 4.0 |
| $Al_2O_3$ | LA-6 | 4.6 |
| AVM | — | 6 |
| Anodized Al | — | 6.3 |
| $Cr_2O_3$ | LC-4 | 8 |
| Stainless Steel | — | 9 |

The coating is preferably deposited on a metallic substrate, which is in the physical configuration of the desired instrument, by means of a detonation gun process. The substrate can be a commercially available instrument or it can be manufactured specifically for this purpose. Other forms of deposition such as arc discharge or plasma torch can also be used.

The thickness of the coating is critical to producing acceptable surgical instruments. Reflectance is reduced as the thickness of the coating increases. However, if the coating is too thick, its upper portion is adversely affected by the heat of the laser beam. This can lead to the flaking off of a portion of the coating. Obviously, this situation is to be avoided as the instruments are used within open incisions.

This condition can be eliminated by keeping the coating thin and thus allowing the metallic substrate to act as a heat sink preventing the coating from overheating. As is readily seen, these two variables require compromise in the design of the thickness of the coating. The coating must be thick enough to reduce reflection adequately, but not so thick as to create problems with excessive heating of the surface of the coating.

The thickness of the ceramic coating should be from about 0.0005 inches to about 0.008 inches. Preferably, the coating should be between about 0.001 inches and about 0.004 inches thick. Most preferred is about 0.0015 inches. Coatings of this thickness ensure that the substrate will serve as a heat sink and draw heat away from the surface of the coating into the substrate. This thickness level provides a substantial reduction in reflection (85% to 99+%) of applied laser energy without any flaking or dislodging of the coating. The desired thickness of the coating is in part determined by the size of the instrument as it relates to the effectiveness of the heat sinking phenomena.

The coating thickness may vary from coating material to material, but in general the heat sinking phenomena must take place or the coating's mechanical properties will be adversely affected resulting in flaking and chipping of the coating.

The adhesion of the coatings to the substrate is of course paramount. Preparation of the surface of the substrate is an important part of obtaining good adhesion. For example, the surface of the substrate is preferably grit blasted prior to the coating, resulting in better adherence of the coating to the substrate.

Alternatively the same effect can be obtained by surface treatment merely deleting a portion of the polishing normally carried out on the surface of surgical instruments. This expedient reduces the cost of the instrument substrate and results in a surface to which the coating readily adheres.

The coating texture is important to the proper functioning of the instrument. Porous coatings ensure that the small portion of the beam reflected will be diffuse and therefore harmless. Glazed or polished coatings can atually increase reflectance and such a reflected beam is specular and thus more dangerous.

A final consideration is that the coating not produce harmful vapors when exposed to the laser beam. The materials used in the present invention may, upon initial exposure to a laser beam, produce small amounts of vapor. These vapors have been tested via atomic absorption spectophotometry and the chemical constituents catalogued. None of the materials used in the present invention produces vapors containing constituents constituting health hazards. In fact, each of the constituents have been found to be at least 1000 times less than the present OSHA limits.

Steps can be taken to reduce vapor production further if desired. These include exposing the coated instruments to laser radiation prior to use, thus freeing the coating of vaporizable constituents or vacuum baking of the instrument to remove the vaporizable components.

The foregoing description has been made with respect to instruments for use in surgery. However, many of the same problems, particularly the necessity of nonreflectance, exist in other technologies utilizing instruments or tools in conjunction with lasers. The inventive concept described above is equally applicable to these nonmedical applications.

Modifications and variations of the invention will be apparent to those skilled in the art. Applicant's intention is to cover all such equivalent modifications and variations as fall within the true spirit and scope of the invention.

What is claimed is:

1. A non-reflective surgical instrument comprising:
   a surgical instrument metallic substrate; and
   a non-reflective coating comprising of a mixture of about 60% $Al_2O_3$ and about 40% TiO by weight deposited on said instrument by a detonation gun process and rendering said instrument substantially non-reflective of infrared radiation.

2. A non-reflective surgical instrument comprising:
   a surgical instrument metallic substrate; and
   a non-reflective coating comprising a $Al_2O_3/TiO$ mixture deposited on said substrate, said coating rendering said instrument substantially non-reflective of infrared radiation.

3. The instrument of claim 2 wherein said $Al_2O_3/TiO$ mixture is about 60% $Al_2O_3$ and about 40% TiO.

* * * * *